(12) United States Patent
Shields et al.

(10) Patent No.: US 11,763,949 B1
(45) Date of Patent: Sep. 19, 2023

(54) COMPUTER-BASED TOOLS AND TECHNIQUES FOR OPTIMIZING EMERGENCY MEDICAL TREATMENT

(71) Applicant: Allegheny Singer Research Institute, Pittsburgh, PA (US)

(72) Inventors: Kelly J. Shields, Pittsburgh, PA (US); John O'Neill, Pittsburgh, PA (US); Charles A. Ferrick, Pittsburgh, PA (US); Shailja Somani, Pittsburgh, PA (US); Philip Nawrocki, Pittsburgh, PA (US); Shiv Dua, Pittsburgh, PA (US); Frances Philp, Pittsburgh, PA (US)

( * ) Notice: Subject to any disclaimer, the term of this patent is extended or adjusted under 35 U.S.C. 154(b) by 0 days.

(21) Appl. No.: 17/590,170

(22) Filed: Feb. 1, 2022

(51) Int. Cl.
*G16H 50/20* (2018.01)
*G16H 40/63* (2018.01)
(Continued)

(52) U.S. Cl.
CPC ............ *G16H 50/20* (2018.01); *G06F 40/174* (2020.01); *G06F 40/205* (2020.01); *G10L 15/22* (2013.01);
(Continued)

(58) Field of Classification Search
CPC ........ G16H 50/20; G16H 40/63; G16H 10/60; G06F 40/174; G06F 40/205; G10L 15/22; G10L 15/26
See application file for complete search history.

(56) References Cited

U.S. PATENT DOCUMENTS

| | | |
|---|---|---|
| 6,842,877 B2 | 1/2005 | Robarts et al. |
| 7,091,851 B2 | 8/2006 | Mason et al. |
| (Continued) | | |

FOREIGN PATENT DOCUMENTS

| | | | |
|---|---|---|---|
| CN | 104485105 B | | 4/2015 |
| JP | 2004046450 | * | 2/2004 |
| JP | 2022529276 A | | 6/2022 |

OTHER PUBLICATIONS

Georgia Institute of Technology, "Wearable device could help EMTS, surgeons assess hemorrhage blood loss", Science Daily, Aug. 31, 2020.
(Continued)

*Primary Examiner* — Tom Y Lu
(74) *Attorney, Agent, or Firm* — Michael D. Lazzara; Leech Tishman Fuscaldo & Lamp

(57) ABSTRACT

An emergency medical treatment system is provided that can be used in connection with providing prehospital medical treatment to a patient. The system includes a patient data display device programmed to receive and display data associated with the patient; an environmental assessment device configured to capture visual, aural, or other ambient environmental data associated with an emergency treatment site associated with the patient; a patient monitoring device configured to be positioned on the patient and having multiple sensors programmed to collect physiological data or vitals data associated with the patient; and a patient data processing device configured with a speech-to-text module. Rules-based or machine learning based algorithm modules can be provided for generating alerts or making treatment option recommendations in connection with the patient data collected and displayed on the patient display device.

26 Claims, 18 Drawing Sheets

(51) Int. Cl.
*G10L 15/26* (2006.01)
*G06F 40/174* (2020.01)
*G10L 15/22* (2006.01)
*G06F 40/205* (2020.01)
*G16H 10/60* (2018.01)

(52) U.S. Cl.
CPC ............ *G10L 15/26* (2013.01); *G16H 40/63* (2018.01); *G16H 10/60* (2018.01)

(56) References Cited

U.S. PATENT DOCUMENTS

| | | | |
|---|---|---|---|
| 7,545,263 | B2 | 6/2009 | Plocher et al. |
| 8,738,396 | B2 | 5/2014 | Green, III et al. |
| 9,569,593 | B2 | 2/2017 | Casella Dos Santos |
| 10,896,678 | B2 | 1/2021 | Ogawa et al. |
| 2012/0078662 | A1 | 3/2012 | Olivarez |
| 2017/0154160 | A1* | 6/2017 | Walker .................. G16H 40/67 |
| 2018/0018590 | A1* | 1/2018 | Szeto .................... G06N 20/10 |
| 2019/0343727 | A1* | 11/2019 | Schulz ....................... A61J 1/16 |
| 2019/0370687 | A1* | 12/2019 | Pezzillo .................. H04L 67/10 |
| 2020/0342968 | A1* | 10/2020 | Avinash ............... G06N 3/0454 |

OTHER PUBLICATIONS

Blomberg et al., "Machine learning as a supportive tool to recognize cardiac arrest in emergency calls", European Resuscitation Council, Resuscitation 138 (2019), p. 322-329.

Kim et al., "A data-driven artificial intelligence model for remote triage in the prehospital environment", PLOS One, 2018, 13(10).
Wu et al., "Strems: A Smart Real-Time Solution toward Enhancing EMS Prehospital Quality", IEEE, 2017.
Nakada et al., "Development of a prehospital vital signs chart sharing system", American Journal of Emergency Medicine, 34 (2016) p. 88-92.
Killeen et al., "A Wireless First Responder Handheld Device for Rapid Triage, Patient Assessment and Documentation during Mass Casualty Incidents", AMIA Annu Symp Proc 2006, p. 429-433.
Nakae et al., "Smartphone-assisted Prehospital Medical Information System for Analyzing Data on Prehospital Stroke Care", American Heart Association, 45(5), May 2014, p. 1501-1504.
Spangler et al., "A validation of machine learning-based risk scores in the prehospital setting", PLOS ONE, 14(12), 2019, p. 1-18.
Medford-Davis et al., "Which transfers can we avoid: Multi-state analysis of factors associated with discharge without procedure after ED to ED transfer for traumatic injury", American Journal of Emergency Medicine, 36(2018), p. 797-803.
Miliard et al., "New partnership brings artificial intelligence to ambulances, paramedics", Healthcare IT News, Mar. 29, 2017.
Evena Medical, "Evena Medical Launches Augmented Reality Glasses Platform", Evena Medical, Nov. 14, 2016.
EMS 1, " 5 wearable technologies for Ems", EMS 1, Mar. 11, 2014.
Gao et al., "The Advanced Health and Disaster Aid Network: A Light-Weight Wireless Medical System for Triage" IEEE Transactions on Biomedical Circuits and Systems, vol. 1 No. 3, Sep. 2007.
Zoll Medical Corporation, "What is the LifeVest Wearable Defibrillator?", Zoll Medical Corporation, 2023.

\* cited by examiner

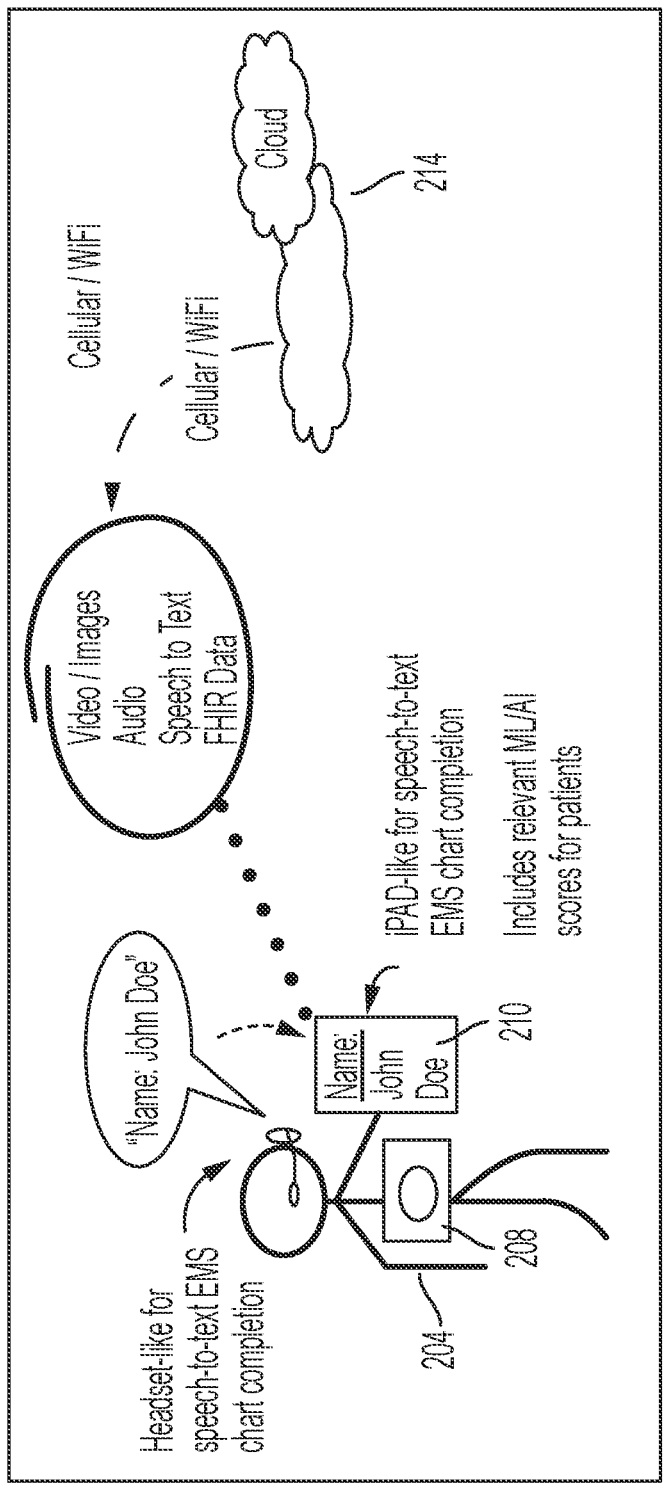

Speech-to-Text Fields

| Field | Keywords | Range of Values |
|---|---|---|
| Name | Patient Name, Name | |
| Date of Birth | Date of Birth, DOB | |
| GCS | GCS | 0-15 |
| Level of Consciousness | Level of Consciousness, LOC | 1. Alert/Alert and Oriented<br>2. Responsive to Verbal Stimuli<br>3. Responsive to Painful Stimuli<br>4. Unresponsive |
| Blood Glucose Level | Gluc, Glucose, Blood Glucose Level, BGL | • Approx. 30 to 500 in most patients<br>• Theoretically, 0 to 2,460 (those levels have been recorded in patients who have survived) |
| Allergies | | |
| Medications | Medications, Meds | |

FIG. 10B

| Rule-Based Algorithms | ML Algorithms (or Combination of ML & Rule-Based) |
|---|---|
| Medication Contraindications | Risk Scores (AMI, Sepsis, Stroke, etc) & If Alerts Needed to be Sent to Hospital |
| Medication Dosage | ED Destination |
| Triage Categories | Primary vs. Comprehensive Stroke Center Needed |
| When to Consult with MD | Use Scene Information to Identify Mechanism of Injury & Severity (ex: photos of car crashes) |
| Termination of Resuscitation | Use Scene/Bystander Information to flag possibility of underlying issues, such as mental illness |
| When Patients can Refuse Care | If C-Spine Precautions are Needed |
| Calculate GCS | |

COMPUTER-BASED TOOLS AND TECHNIQUES FOR OPTIMIZING EMERGENCY MEDICAL TREATMENT

FIELD OF THE INVENTION

In various embodiments, the present invention generally relates to computer-based tools, devices, and processes for assessing patient health status, analyzing patient data, electronically transferring high-value patient data, and administering medical treatment to patients. In particular embodiments, the invention relates to collecting and analyzing patient data derived from a prehospital emergency medical treatment environment.

BACKGROUND

Providing adequate health care is an essential component of promoting the wellness, productivity, and general standard of life of people living in a community. It is especially important to provide Emergency Medical Services (EMS) urgently and effectively for individuals who are in crisis situations.

Emergency Medical Technicians (EMTs) and paramedics arriving on an emergency scene need to quickly ingest as much information as possible regarding the patient, including the scene/site description, patient medical history, information from the patient's family, friends or bystanders, as well as discrete vital information. Typically, this information must be manually entered into an electronic device or documented on paper for later electronic recording. The patient is then transported to the most appropriate Emergency Department (ED) of a hospital facility. During patient transport, the EMT or paramedic considers trauma level, specialty care, and other ED-specific considerations, while continually monitoring and stabilizing the patient. This happens while the EMT/paramedic is also attempting to manually document critical information into an electronic device or laptop. In addition, EMS providers may need to call an ED doctor, poison control, and/or their EMS agency to consult in certain situations. EMS providers are often expected to accurately and completely explain the full patient situation to these entities and agencies and receive direction while continuing to provide patient care. When the EMS team arrives at the hospital, they often convey critical patient information to the ED health care team via a handwritten short form. These conventional data collection and analysis methods can negatively impact the efficiency and effectiveness of health care, especially for patients in need of emergency medical treatment.

What are needed, therefore, are improved computer-implemented techniques, devices, and tools that can more effectively collect, transfer, analyze, and process data for patients in need of health care. Such techniques and tools are especially needed to improve the efficiency and effectiveness of providing emergency medical treatment for patients.

BRIEF DESCRIPTION OF THE FIGURES

FIG. 8 through 10B show different aspects of examples of speech-to-text conversion functionality configured in accordance with certain embodiments of the invention.

FIG. 13 includes a table illustrating examples of various medical or health care situations to which rules-based algorithms and/or machine learning algorithms may be applied.

DESCRIPTION

Figure 1:
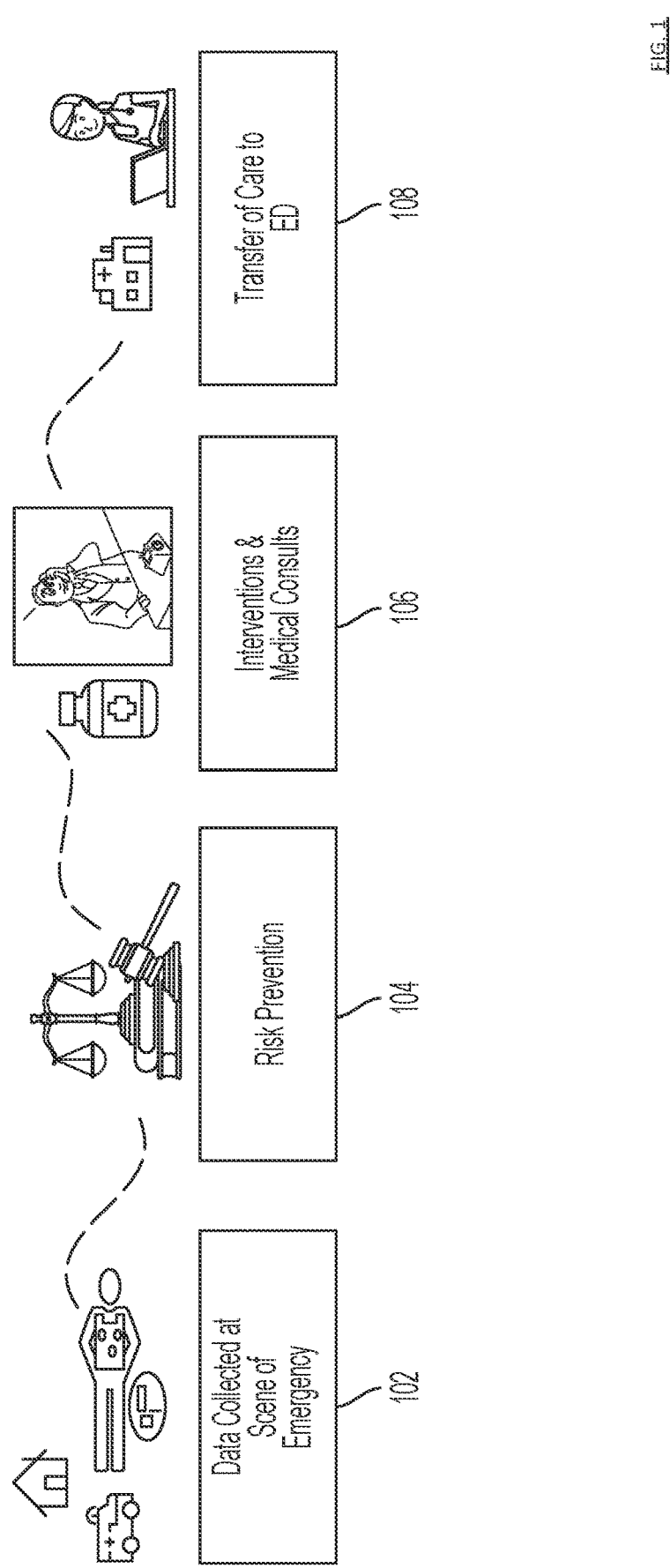
FIG. 1 includes an overview of various parts of the process which represent opportunities for technological implementations in a prehospital environment.

In developing the various embodiments of the invention described herein, the inventors have appreciated the need for advanced technology for providing health care to patients in the prehospital environment prior to their admission into a hospital or medical facility, for example. As applied herein, a "prehospital" environment may include any initial medical care given an ill or injured patient by an EMS provider or other person before the patient reaches a hospital emergency department. For example, the prehospital environment may include a patient residence, roadways for automobile accidents, crime scenes, or mass casualty incident (MCI) scenes, among other locations where patients require emergency medical treatment. Those skilled in the art can appreciate that embodiments of the invention described herein may be equally applicable to other medical treatment or healthcare environments other than prehospital environments, including in-hospital, residential, or home health care environments, for example. For example, various tools and components described herein may be used for non-emergency prescribed patient treatment purposes or for non-emergency preventative patient care, among other possible uses.

In certain aspects of the invention described below, it can be seen how the ability for the EMS/prehospital team to have an automated and less manually intensive way of communicating important patient information, including auto-generation of necessary medical documents, improves patient assessment, medical treatment, and overall efficiency of the process. Collecting and analyzing physiological vital data in real-time allows for improved history of the patient throughout the treatment process extending from the emergency scene to the hospital and more seamless communication of essential information to the Emergency Department (ED) and the patient's electronic health record (EHR). The use of tools and devices such as body cameras and microphones configured to capture video data, image data, and sounds or acoustical data can improve patient and scene assessments which need to be made at the emergency site, in the ED, and also for recall and potentially training new EMS/prehospital teams, as well as for reference in case of legal or evidentiary issues arising from EMS service. The acquired data, which in some embodiments can be coupled with HL7 FHIR capabilities, for example, facilitates the execution of more robust rules-based and machine learning algorithms which aid in potentially life-saving decisions. In various aspects, collection and storage of such data enables EMS assessments and prehospital assessments of patient outcomes for purposes of process improvement, training, and research, among other useful benefits.

In various embodiments, the present invention provides enhancements over essential information/data collection and processing limitations and augments medical treatments by using different features (or a combination thereof). In one aspect, wearable vital sensor devices (one example is a "Vital Vest" device described herein) can be equipped on or worn by a patient. These vital sensor devices can be configured to collect patient data such as, but not limited to, body temperature, blood oxygen, respiration, heart rate, blood pressure, electrocardiogram, and/or blood glucose levels, among others, using continuous or near-continuous patient data feeds. In other aspects, speech-to-text functionality can be provided for the EMS/prehospital team to have hands-free or less manually intensive capabilities to enter the scene information and critical patient information to complete an EMS Patient Care Record (PCR), as well as to collect any information communicated by patients, bystanders, or others at the emergency site.

Electronic transmission of recorded EMS data and user-entered EMS data can be communicated to computer systems operatively associated with the receiving ED, as well as the EMS agency, thereby minimizing data loss. In other aspects, body cameras or other user devices capable of continuous or discrete image/audio capture can be used by EMS personnel in assessing a patient at an emergency site, for example. Data connectivity to HL7 FHIR data can be provided for generating a more complete medical history for the patient (e.g., previous EMS incidents and/or EHR data), which can assist with administering medical treatment to the patient. It can be appreciated that the data can be ingested and processed in a targeted way, such as by organization or display of the data, to make the data more readily usable for purposes of providing effective health care to patients. In certain aspects, rules-based and machine learning algorithms can be employed which are capable of alerting EMS personnel or others to various situations such as, but not limited to, medication contraindications, most appropriate ED destination, requirements for certain protocols (e.g., termination of resuscitation), triage levels in the event of multi-casualty incidents, patient deterioration scores, etc. Such algorithms can be used to optimize patient care by minimizing human error or bias which might arise in connection with medical treatment. For example, EMS personnel might have a bias or might make a suboptimal judgement call about the optimal ED to which a patient should be transported from the emergency site. The algorithms can be used to drive better decisions based on patient care by employing a data-driven and analytical approach to such decisions.

In certain embodiments, the system and devices described herein can maximize the opportunity to record vital physiological data, video/images, and audio during the time extending from EMS arrival at an emergency site, through patient transportation, and ending with patient arrival at the ED of a facility. Vital physiological data can be collected during this time which can be used for generating real-time EMS dashboards, transferring data to ED/hospital EHR computer systems, communicating recent or long-term history of the patient for ED use, and for improving prehospital and hospital patient care by using such data as input for rules-based and machine learning algorithms. The data collection, dashboards, real-time use and history may prove critical in decision making as care is transitioned to ED/hospital facility. Vital physiological data can be used in rules-based and machine learning algorithms for evaluating physiological phenomena such as, but not limited to, patient deterioration, best ED destination for certain conditions, medication dosage, triage category, the need to call in alerts, such as but not limited to a stroke alert or best practices of treatment for certain conditions. The rules-based and machine learning algorithms may be augmented with video data, audio data, voice or verbalization data, and/or acoustical data (e.g., ambient environment noises), such as patient breathing sounds, patient voice volume, physiological sounds (e.g., heart beating, lung noises, coughing, wheezing, digestion noises), or any other audible data which might be clinically relevant. Also, the devices may be configured to be HL7 FHIR compliant with the capability to provide additional information for real-time decision making and augmentation of the rules-based and machine learning algorithms.

The inventors have recognized that prior to the development of their invention there have been insufficient relevant technological advances in the prehospital space. In various embodiments, the present invention offers enhanced features in connection with data collection, data entry, rules-based and machine learning algorithms, and EHR-data communications to the ED, among other important components of the overall emergency medical treatment process.

FIG. 1 includes an overview of examples of various parts of this process which represent opportunities for technological implementations in a prehospital environment. In one example, at stage 102, technology can be used to enhance data collection processes at the site of the patient emergency. Vitals data for the patient (e.g., ECG, hear rate, blood pressure, blood oxygen, respiration rate, and others) can be collected at this stage, as well as data associated with images, sounds, speech, or other perceivable aspects of the emergency treatment scene. An electronic chart can be used to process and graphically display different aspects of the collected data. At stage 104, risk prevention can be promoted by identifying comparatively higher risk situations, such as when a patient has a psychological or behavioral condition that must be considered in connection with providing proper medical treatment. Risk prevention can also involve collecting and processing data which assists with determining whether or not a refusal to accept medical care can be honored. At stage 106, enhanced medical care can be performed in real-time for a patient, such as allowing a physician, poison control, etc., to view a patient's EMS chart in real-time if an online medical consult is needed, to recommend an appropriate medicine dosage, to intervene when an otherwise routinely recommended course of treatment for a particular patient is actually contraindicated for that patient, and/or to chart medical care actions for the patient with speech-to-text functionality. In another aspect, at stage 108, certain embodiments of the present invention can aid in the decision involved with identifying a proper ED or hospital facility to which the patient is to be transferred. For example, EMS providers can be aided in this decision by algorithms which would considering hospital capacities, trauma levels/specialty centers, distance to hospitals, patient condition and deterioration, patient medical history and more. Throughout medical consultations and upon arrival to the ED, the use of a cloud-based electronic interface would allow for the ability to capture instructions, approvals and transfer of care by electronic signature, for example. This can facilitate providing a substantially seamless transfer of care for the patient to the ED, or for transferring the patient between health care facilities, as well as decrease potential legal liability for EMS providers.

Figure 2:
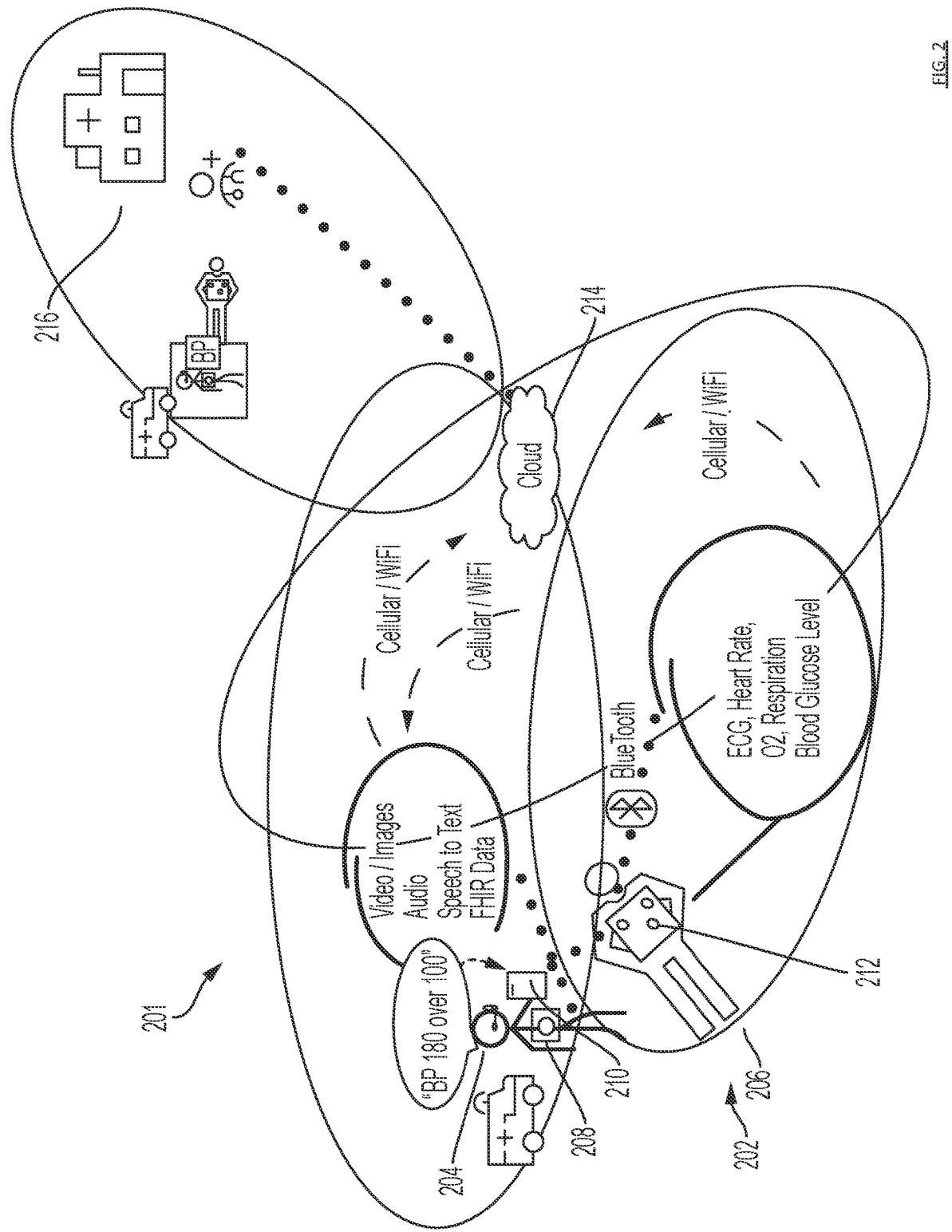
FIG. 2 schematically illustrates one example of an emergency medical treatment system and associated process and data flows structured in accordance with various embodiments of the invention.

FIG. 2 schematically illustrates one example of an emergency medical treatment system 201 structured in accordance with various embodiments of the invention and configured for prehospital patient data collection and processing. As shown, EMS personnel 204 (e.g., an EMT or paramedic) are summoned to the site 202 of an emergency medical situation where a patient 206 needs medical attention. The EMS personnel 204 may be equipped with one or more environmental assessment devices 208 such as a body camera device, for example, configured to capture audio, video, and/or acoustical signals associated with the emergency treatment site 202. The EMS personnel 204 may be further equipped with a patient data display device 210 which is programmed with various features and functions including, for example, processing and displaying speech-to-text form completion features (as described in more detail below). In the example shown, a patient monitoring device 212 (e.g., a "Vital Vest" device) may be positioned on the patient 206 which is programmed to collect physiological or vital signs from the patient 206.

The device 212 can be configured to combine multiple physiological sensors into a wearable vest utilizing short-range wireless or hardwired technology to facilitate continuous or near-continuous collection of vital physiological data such as, but not limited to, body temperature, respiration rate, blood oxygen levels, among other patient 206 physiological conditions. The devices 210, 212 may be configured with short-range wireless technology (e.g., Bluetooth wireless technology) and/or cellular/WiFi capabilities for collecting, communicating, and transferring data, such as to patient care records (PCRs) and/or to data storage within a cloud computing environment 214. In various embodiments, instead of a vest-type device 212, the patient monitoring device 212 may be embodied as a watch, a forehead mounted sensor band, a ring, a belt, a harness, or a variety of other devices which can be configured to include sensors 212 for detecting and collecting signals derived from patient physiological data. In certain embodiments, to provide optimum patient care, a suitable device 212 may be selected in response to characteristics of the patient (e.g., age, physical dimensions, type of injury, body position, etc.), the nature of the emergency treatment site itself (e.g., in a vehicle, on the ground, the terrain, etc.), and/or other factors. In various embodiments, parameters associated with the type and installation of the device 212 can include providing a patient-wearable component which minimizes risks of further injury to the patient 206 while optimizing collection and analysis of patient data. For example, a vest-type device 212 may be configured as a generally rectangular component which lays over the chest of the patient 206, without necessarily being secured to the body of the patient 206. Those skilled in the art will appreciate that selection of an appropriate device 212 can be driven by balancing providing safe and effect health care to the patient 206, while minimizing interference with the current health or medical condition of the patient 206.

Figure 3:
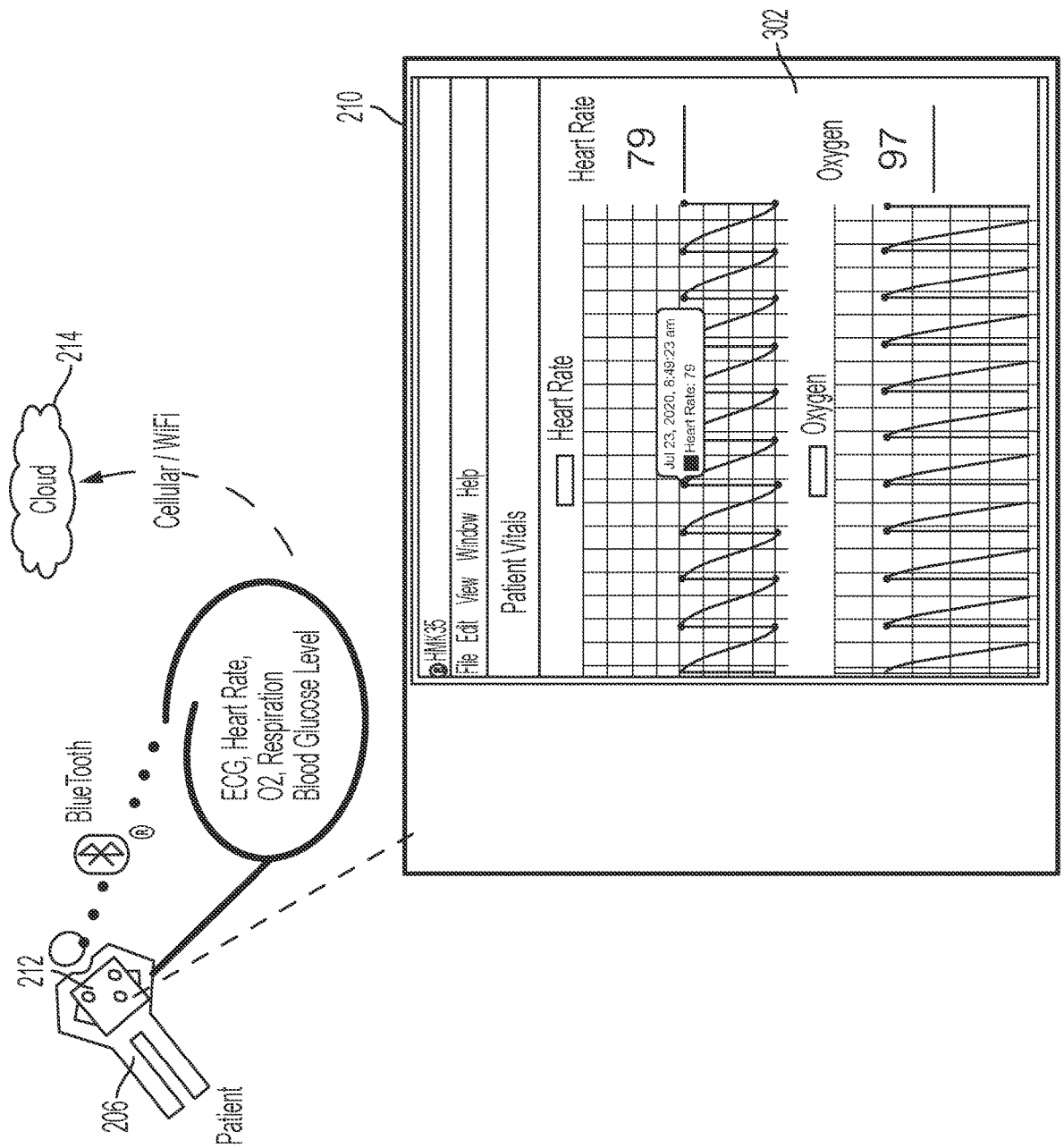
FIG. 3 illustrates one example of a graphical representation of vitals data which can be generated and displayed for a patient on the patient data display device.

In certain embodiments, the cloud computing environment 214 may be operatively associated with HL7 FHIR tools and techniques (Fast Healthcare Interoperability Resources ("FHIR"), including standards developed by Health Level Seven International ("HL7"). These tools and techniques can improve data sharing and assist with building FHIR solutions and applications. Various embodiments of the present invention may use SMART-on-FHIR applications, for example, to access comprehensive patient records. This information, in total, allows for a more in-depth look at the patient, giving a prehospital team a comprehensive look at a patient, which can be critical if the patient is alone or involved in a trauma where there is no representative to speak on their behalf. This type of data can also be used by the rules-based and machine learning algorithms described herein. In another aspect, computer systems of an ED of a hospital or other medical facility 216 may be configured to communicate and process data in connection with the cloud computing environment 214. FIG. 3 illustrates one example of a graphical representation 302 of vitals data which can be generated and displayed on the patient data display device 210 in connection with patient 206 data communicated from the patient monitoring device 212, for example.

Those skilled in the art will appreciate that collecting and processing continuous or near-continuous vital physiological data is valuable for many reasons. For example, real-time vital physiological data can be made available to EMS/prehospital teams for uses including, but limited to, dashboards identifying certain values above or below predefined thresholds, significant changes in vital signs, tracking correlated vital data, and periods of time without a signal, among others. A prehospital history for the patient 206 can be useful for the ED health care team of the facility 216. A biostatistics summary can be generated for the ED health care team to provide a longitudinal evaluation over time that can trigger alerts associated with fluctuations or acute situations occurring during the time prior to patient 206 arrival at the medical facility 216. Communicating continuous or near-continuous graphs of vital data allows for likewise real-time or near real-time trend analysis and is a significant improvement from EMS providers merely communicating a few sets of handwritten vitals, with each measurement perhaps taken 5-10 minutes apart. If the EMS personnel need to consult with ED physicians for medication, protocol, or refusal of care medical direction, physicians in the ED could view the real-time graphs of patient vitals data being pushed to the cloud computing environment 214, rather than relying on a 30-second verbal summary from EMS personnel via radio or phone communication to offer medical direction. In certain embodiments, various components of the system 201 can be programmed for generating, communicating or processing an alert in response to real-time changes detected outside of a predetermined threshold or range for the vital physiological data associated with the patient 206.

In certain embodiments, vitals data (among other types of data) can be used in developing rules-based and machine learning algorithms for alerting the EMS/prehospital team to patient-specific conditions such as, but not limited to, patient deterioration, best practices for certain conditions, most appropriate ED destination, trauma level or specialty care needs. For example, condition alerts may be generated such as for patient 206 conditions including stroke, STEMI alerts, and patient risk for certain conditions (e.g., stroke or MI). The vitals data may be stored in the cloud computing environment 214 to be integrated with the existing or historical EHR data for the patient 206, for example, and/or with new EHR data to be generated as a result of the ED visit. In other aspects, the vitals data may be combined with an HL7 FHIR repository (e.g., previous EMS incidents and/or hospital EHR data) to enhance the rules-based and machine learning algorithms utilizing historical patient 206 data. This allows for improved patient-specific modeling which offers valuable insights and indicators for the health care work performed by the EMS/prehospital team, for example.

Figure 4:
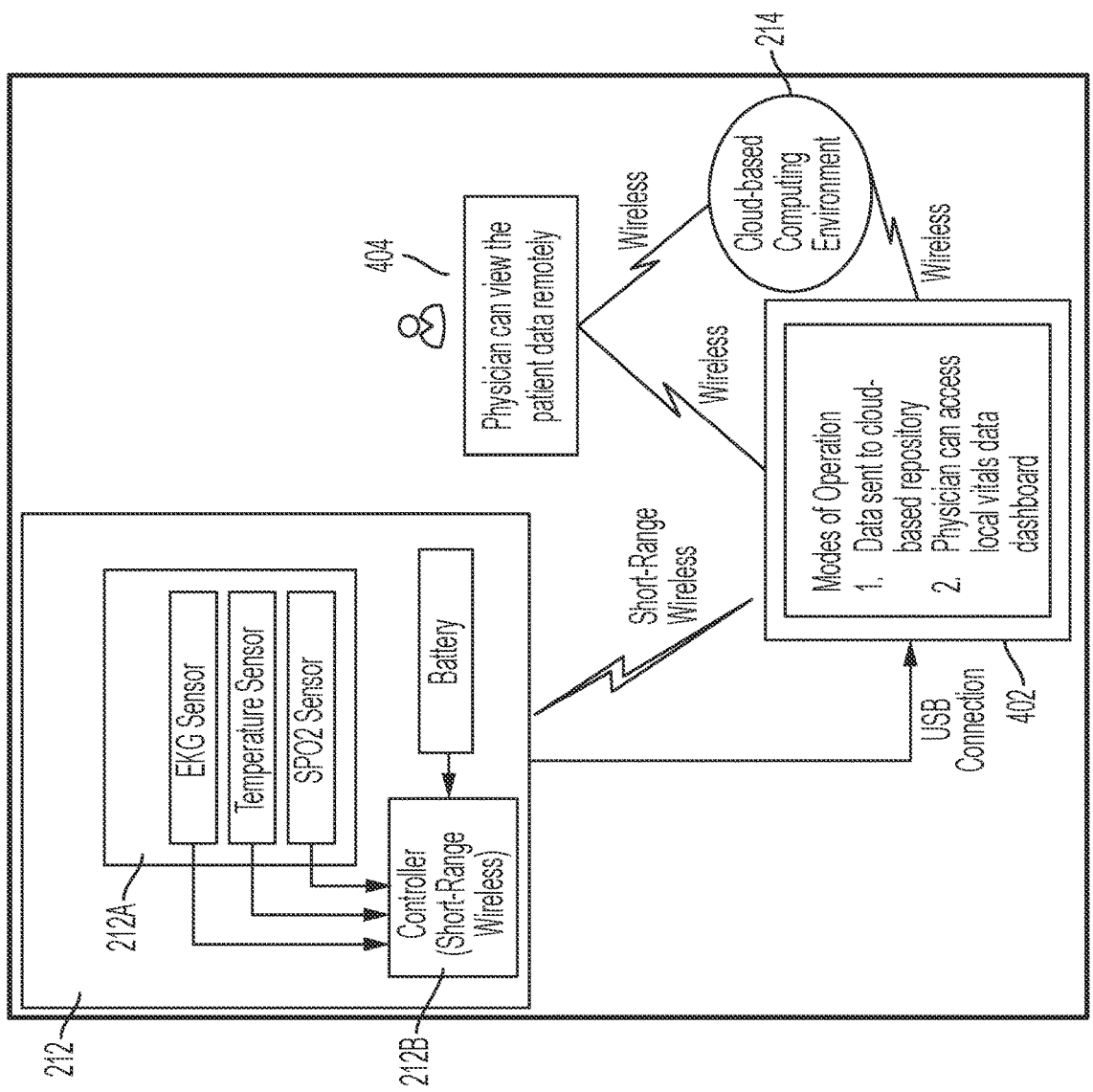
FIGS. 4 and 5 schematically illustrate examples of a patient monitoring device configured for transfer of data to an ED with a patient data processing device in accordance with various embodiments of the invention.
Figure 5:
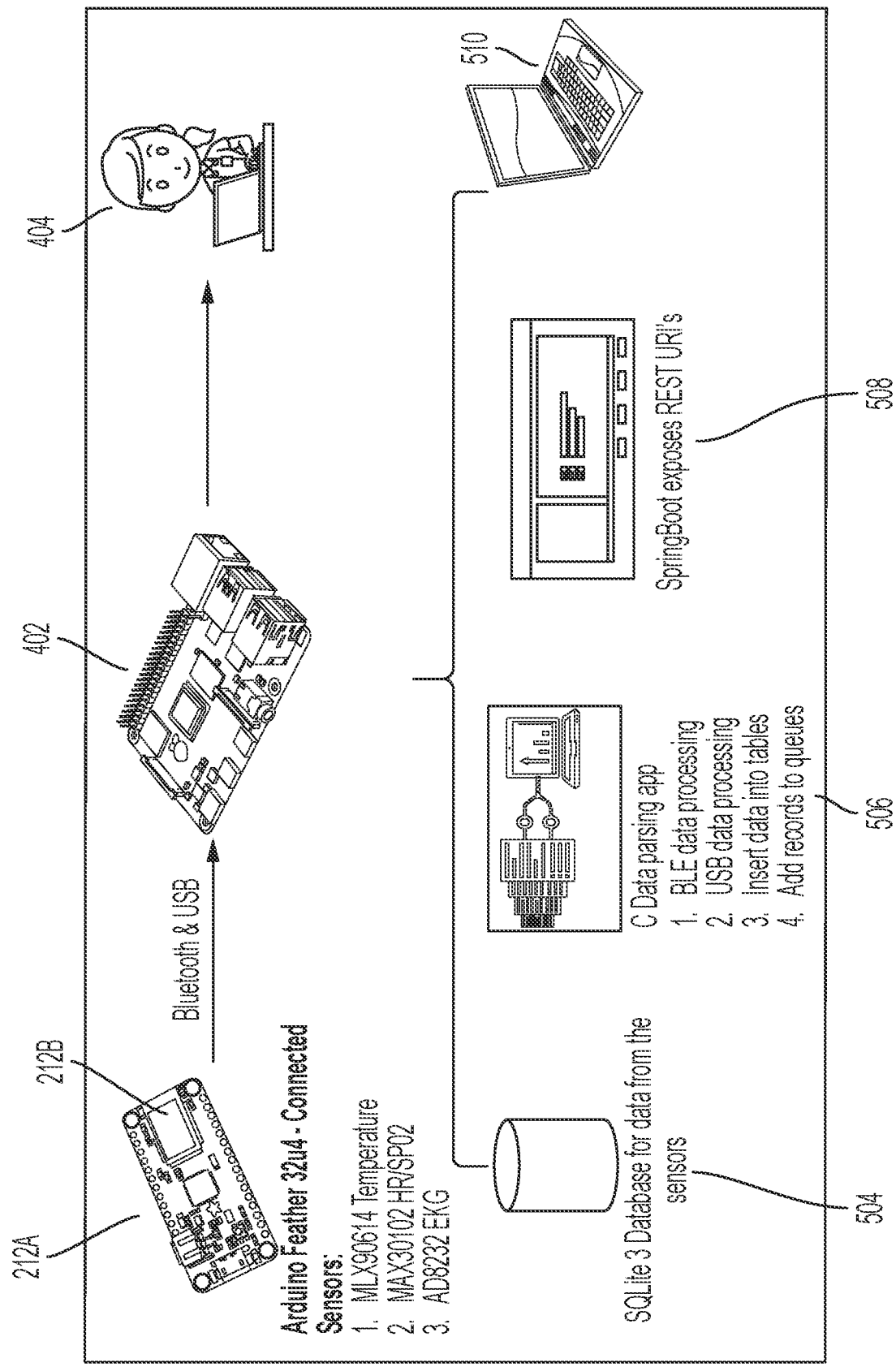

FIGS. 4 and 5 schematically illustrates examples of the configuration of a patient monitoring device 212 and the configuration of a patient data processing device 402 programmed for communication with the device 212. In the example shown, the device 212 includes various sensors 212A for detecting vitals data or other physical conditions of the patient 206. The device 212 also includes a controller 212B enabled with short-range wireless technology and configured to communicate with the device 402. The device 402 can be operatively associated with the patient data display device 210 and/or configured to communicate data for storage in the cloud computing environment 214, for example, and/or to a computer system 404 of a health care practitioner. In one aspect, the device 402 can be configured to present patient 206 data to the computer system 404 in the form of one or more types of user interface screens or dashboards. In certain embodiments, the device 402 may be operatively associated with one or more data storage media 504, such as for storing sensor data communicated from the device 212, for example. The device 402 may employ various kinds of data parsing applications 506, such as for formatting collected data into various kinds of communication protocols or data table structures, for example. In certain embodiments, the device 402 may access different kinds of REST URI applications 508 in connection with communicating patient data to a computer system 404 of a user such as an EMS provider or ED triage nurse, for example. The device 402 may further employ different types of user interface applications 510 for generating and communicating user interface screen displays to the patient data display device 210, the computer system 404, and/or other computing devices.

In certain embodiments, the patient data processing device 402 may include a processor or controller (e.g., a small board computer (SBC) device, such as a "Raspberry Pi" device) for processing data communicated to or form the device 402. It can be seen that the device 402 can act as a central communication processor for the sensors 212A, for collecting cloud-based data, for accessing FHIR tools, for reporting results of execution of rules-based and machine learning algorithms, and for completing forms, among other tasks. In various embodiments, the patient data display device 210 and the device 402 may be combined into a single component or provided as separate components. In the separate component embodiment, the device 210 may be provided as an electronic tablet (e.g., an "iPad" device), for example, equipped with software components programmed for enabling data communication with the device 402. In other embodiments, different features or functions of the devices 210, 402 can be shared or distributed between the different devices 210, 402 in a variety of possible combinations.

In certain aspects, either one or both of the devices 210, 402 may be provided with sufficient backup data storage to facilitate patient data storage in the event of a disruption or discontinuation of data communications. For example, if the emergency treatment site is located in a geographical location with limited or unreliable wireless connectivity, then the backup storage can be engaged to resist loss of collected patient data. In one aspect, the device 402 may be equipped with a global positioning system (GPS) device programmed to determine whether a given emergency treatment site location is associated with insufficient wireless connectivity capability. Upon determination or prediction of wireless capability, the system 201 can be programmed to preemptively notify the device 402 to engage its backup data storage functionality for data collection at that location. In other embodiments, the backup data storage functionality may be enabled whenever either of the devices 210, 402 has been activated. In other aspects, the GPS device may be used to assist with determining an optimum ED location, for example, or other health care facility to which the patient 206 should be transported from the emergency treatment site.

Figure 6:
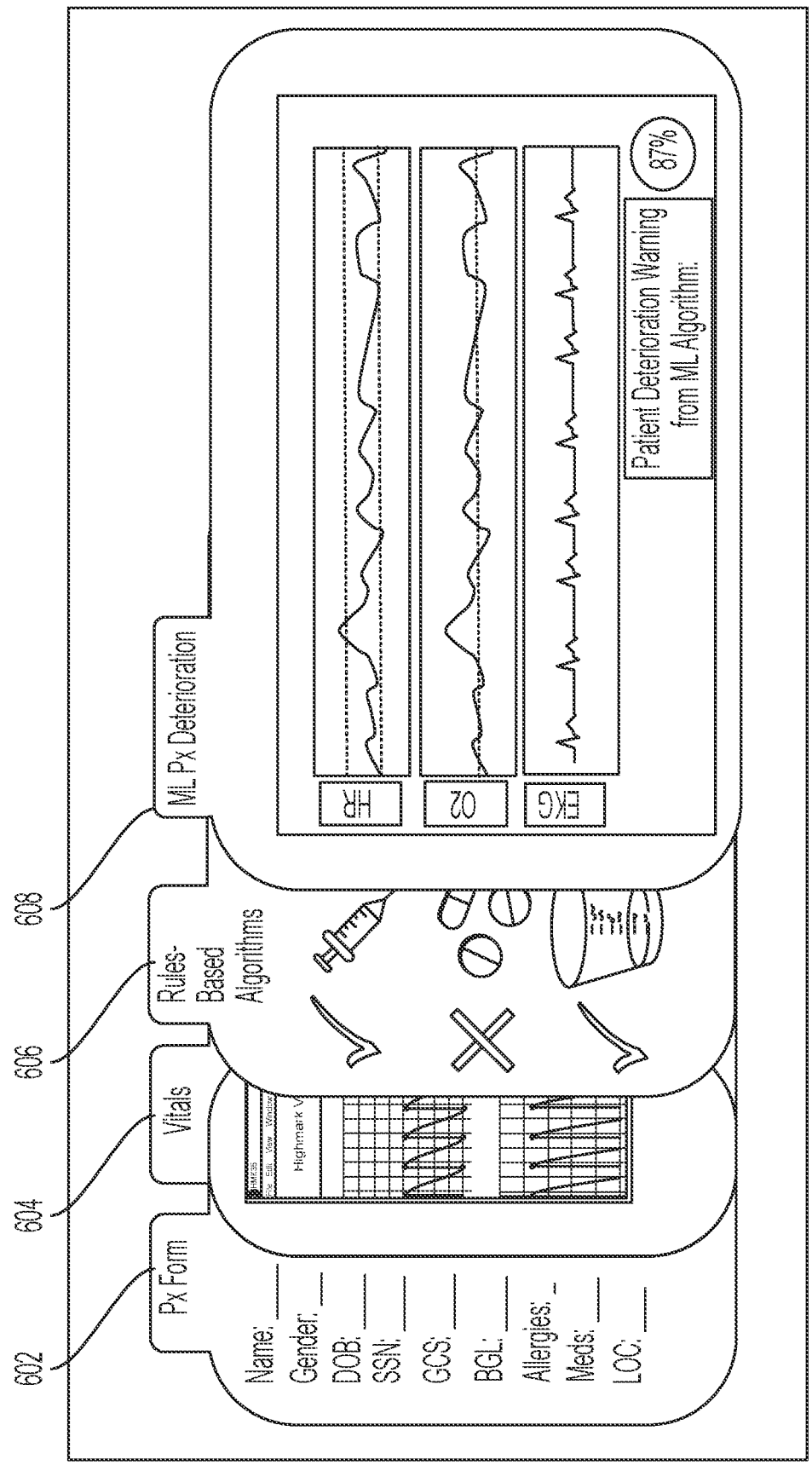
FIG. 6 schematically illustrates examples of user interface screen displays which can be generated and displayed on different devices in accordance with various embodiments of the invention.

FIG. 6 schematically illustrates examples of the user interface screen displays which can be generated and displayed on a patient data display device 210, the computer system 404, and/or to other computing devices. In one example, a Patient History Form (or Px Form) user interface 602 can be used to collect demographic and medical data associated with emergency medical treatment of a patient 206. In another example, a Vitals user interface 604 can be programmed to display vitals data in real-time which may graphically represent patient 206 data collected via the patient data display device 210. A rules-based algorithms user interface 606 can be programmed to present the results of executing an algorithm in connection with determining treatment for the patient 206, such as displaying treatments that may be contraindicated for the patient 206, protocol alerts, or other information. In another aspect, a machine learning algorithm user interface 608 can be used to access and execute various machine learning algorithms and/or present the results of predictive analysis performed by a machine learning algorithm (e.g., patient deterioration analysis).

Figure 7A:
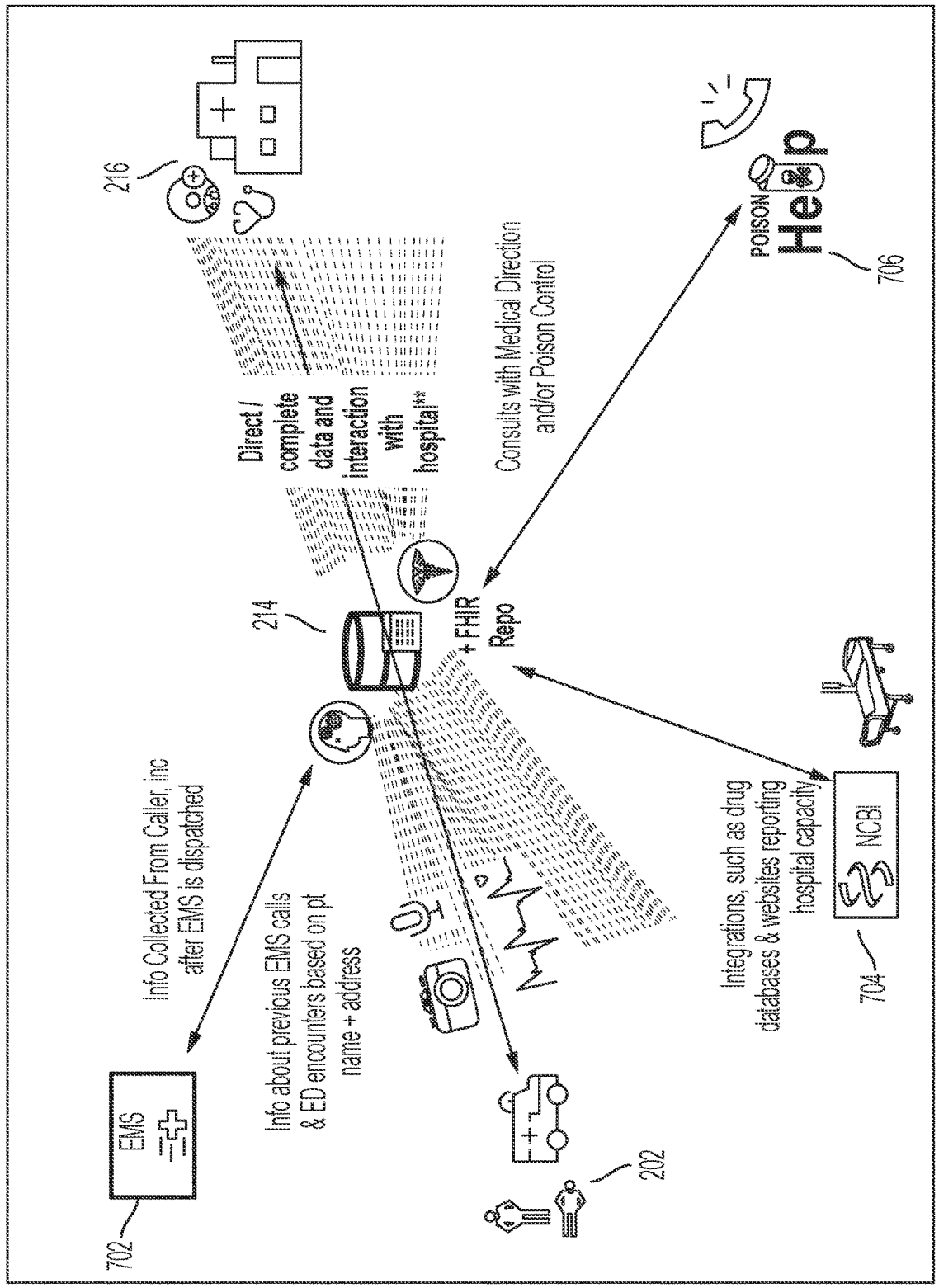
FIG. 7A illustrates a combined computer architecture and process flow diagram depicting one example of data flow between and among different information sources.
Figure 7B:
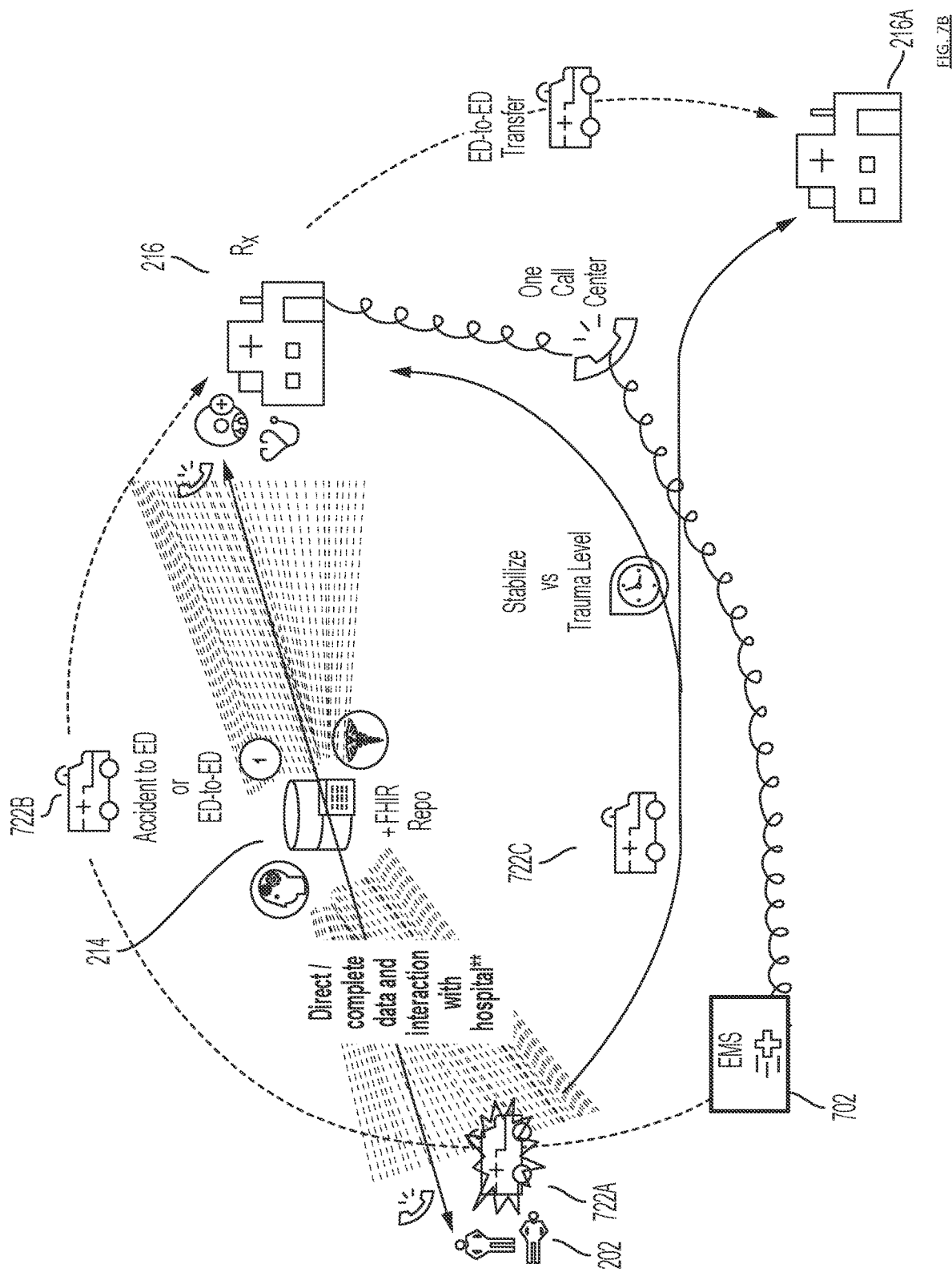
FIG. 7B illustrates a combined computer architecture and process flow diagram depicting another example of data flow between and among different information sources.

FIGS. 7A and 7B include a combined computer architecture and process flow diagram depicting examples of data flow and communications between and among an EMS dispatch center and headquarters 702, an emergency scene 202, publicly available external data sources 704, consultation communications with medical directors 706, and the ED of the hospital 216. Data collected from these different kinds of information sources can be stored within and processed through the cloud computing environment 214, as shown, for performing the various tasks and functions of the system 201, including executing relevant rules-based and machine learning algorithms as described herein. increase data transfer from pre-hospital to facility (electronic rather than handwritten). As shown in FIG. 7B, an ambulance 722A transporting the patient from the emergency scene 202 may be to the hospital 216 via a first route 722B. In another aspect, based on communications with the hospital 216, vitals data gathered for the patient during treatment at the scene 202 or during subsequent transport, or other data communications between or among the entities shown in FIGS. 7A and 7B, the ambulance 722A may be directed along a different route 722C to a different hospital 216A. Such routes 722B, 722C may determined as part of the process of determining an optimal ED destination based on collected and processed patient data.

FIG. 8 through 10B show different aspects of examples of speech-to-text conversion functionality configured as an operative module in accordance with certain embodiments of the invention. In certain embodiments, speech-to-text technology can be used to help the EMS personnel 204 have a substantially hands-free interaction with electronic devices, such as the patient data processing device 402 and/or the patient data display device 410. This allows the EMS personnel 204 to concentrate on providing care to the patient 206 at the emergency treatment site. In certain aspects, this speech-to-text functionality can be used to complete necessary medical forms that could then be communicated and incorporated into an EHR system, for example. Any HL7 FIHR data available for the patient 206 (and permissible for EMS providers to view) can be incorporated as a history section of the PCR. This data can further be made available to the EMS personnel 204 and ED teams at the hospital 216 to provide more personalized and appropriate care along with features to be added to either rules-based or ML-based algorithms.

Figure 8:
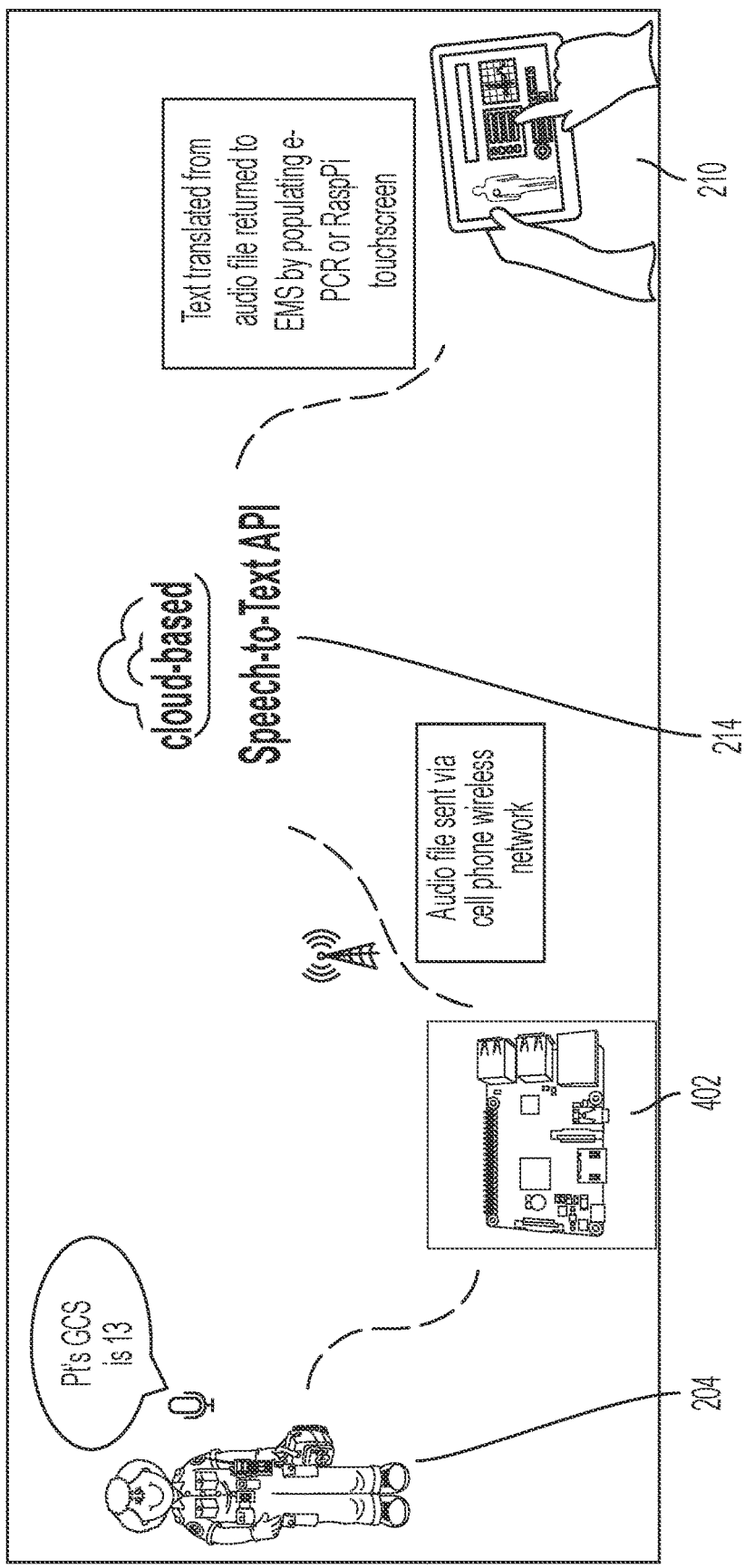
Figure 10A:
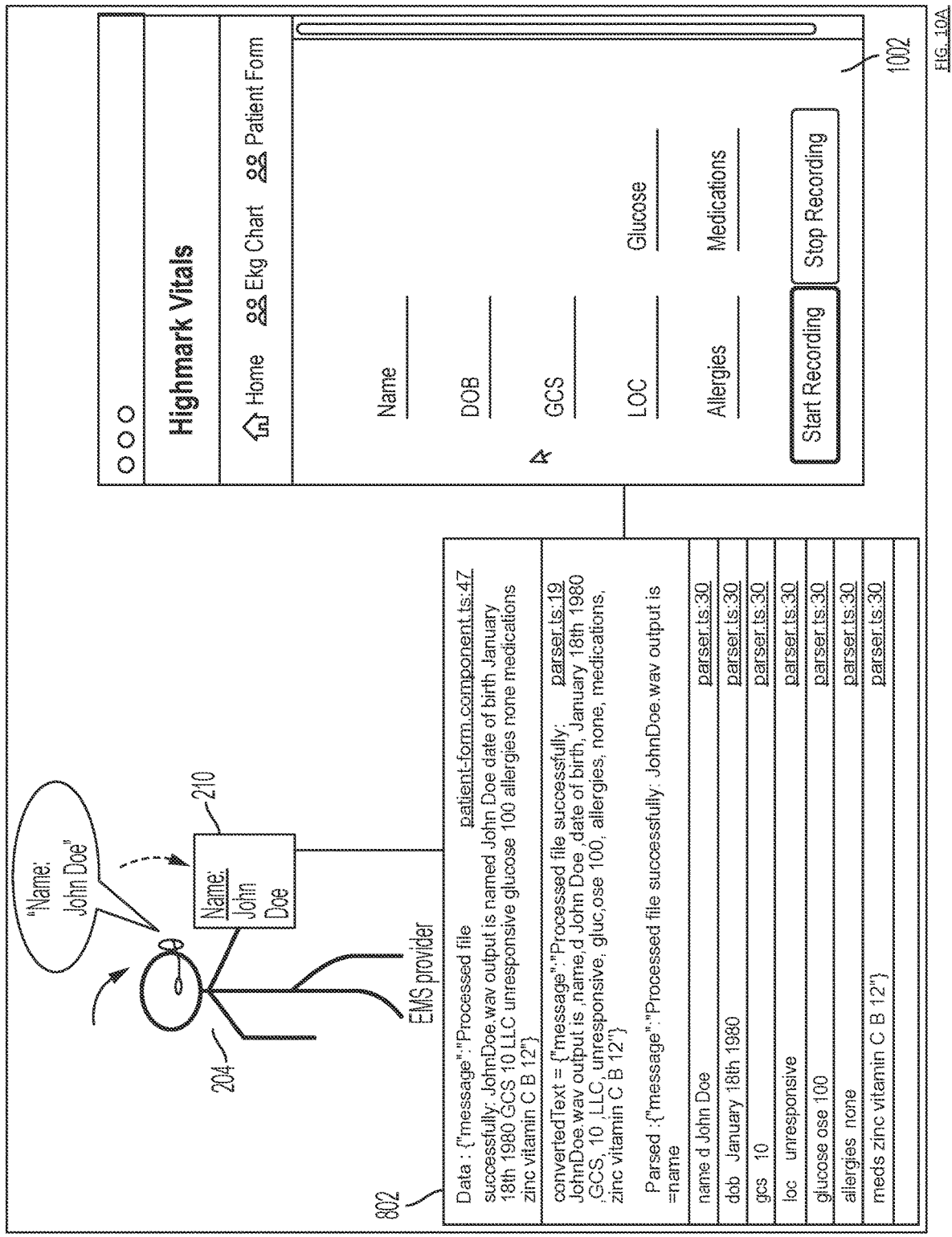

As shown by the example illustrated in FIG. 8, the EMS personnel 204 verbally articulates that the Glasgow Coma Scale (GCS) score of the patient 206 is at a level of 13. The device 402 records this statement and generates and communicates an audio file to the cloud computing environment 214, wherein a speech-to-text application program interface (API) can be executed to convert the audio file into text. The converted text file can be communicated back to the devices 402, 210, and the text can be auto-filled into a screen display showing the text in a form or the PCR record 1002 for the patient 206. The text can be parsed by a text parsing application 802, for example (see FIG. 10A). The newly populated data can be used for executing rules-based and ML-based algorithms and for generating a complete electronic record of the patient 206 in the prehospital environment to be used by the hospital 216 in the future. It can be seen how pertinent fields of different forms which are required to complete the PCR can be automatically populated without interrupting patient care. FIG. 10B includes a table illustrating various examples of speech-to-text fields which can be populated, including the type of data field, the keywords which can be detected for each data field, and the expected verbal input which can be detected and processed as part of the speech-to-text conversion process. It can be appreciated how this speech-to-text feature can significantly reduce data lost due to the nature of chaotic environments associated with providing emergency medical treatment, which often includes manually completing a short form with patient information to hand off to triage at the ED, for example.

Figure 11A:
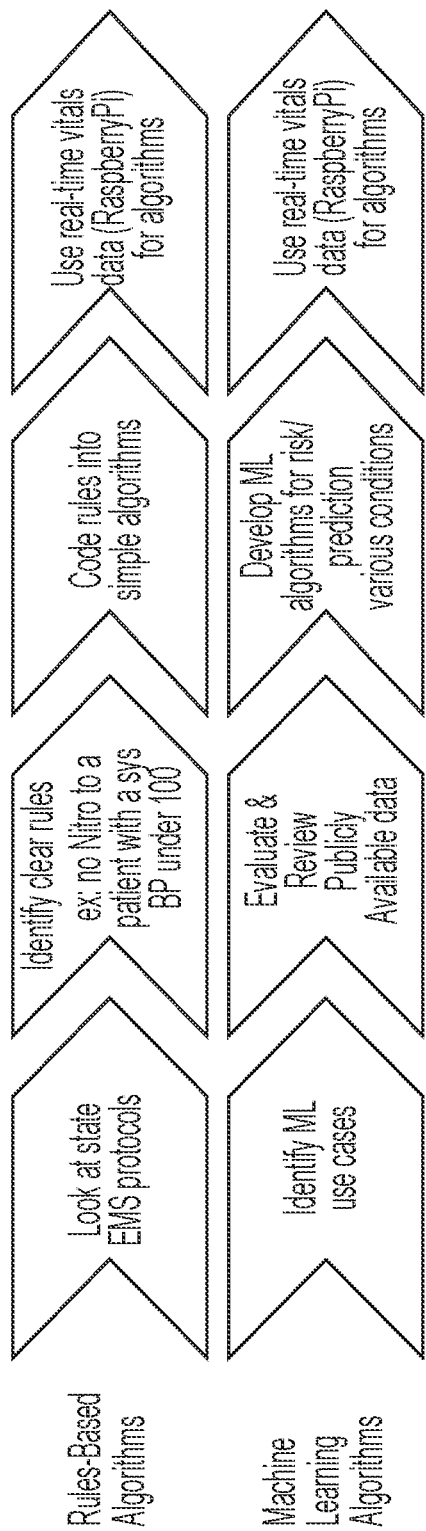
FIG. 11A schematically shows a process flow for development of machine learning based and rules-based algorithms in accordance with certain embodiments of the invention.

FIG. 11A includes a process flow illustrating a development process for creating machine learning based and rules-based algorithms in accordance with certain embodiments of the invention.

Figure 11B:
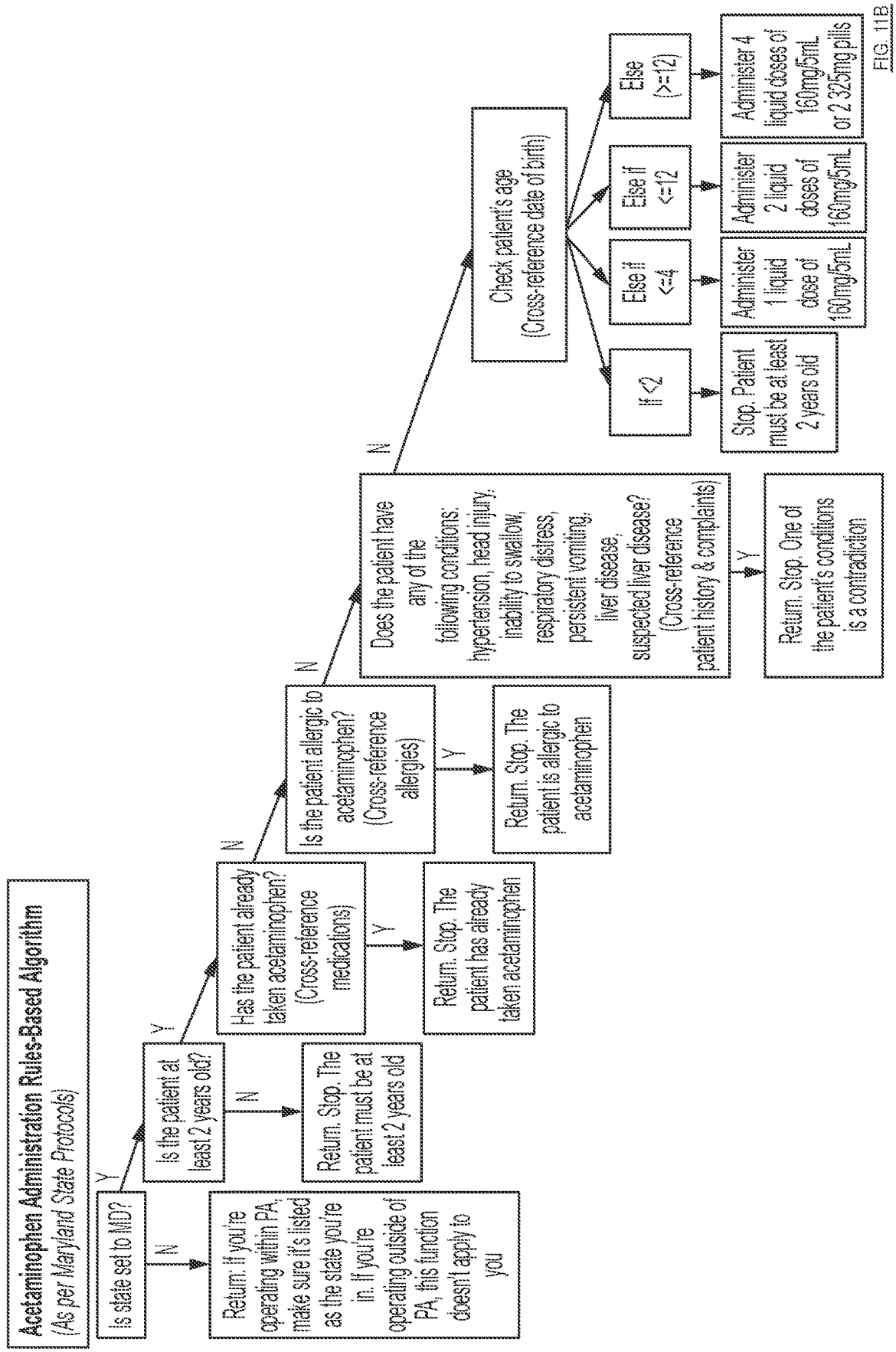
FIG. 11B includes a process flow diagram illustrating an example of the execution of a rules-based algorithm in accordance with certain embodiments of the invention.
Figure 11C:
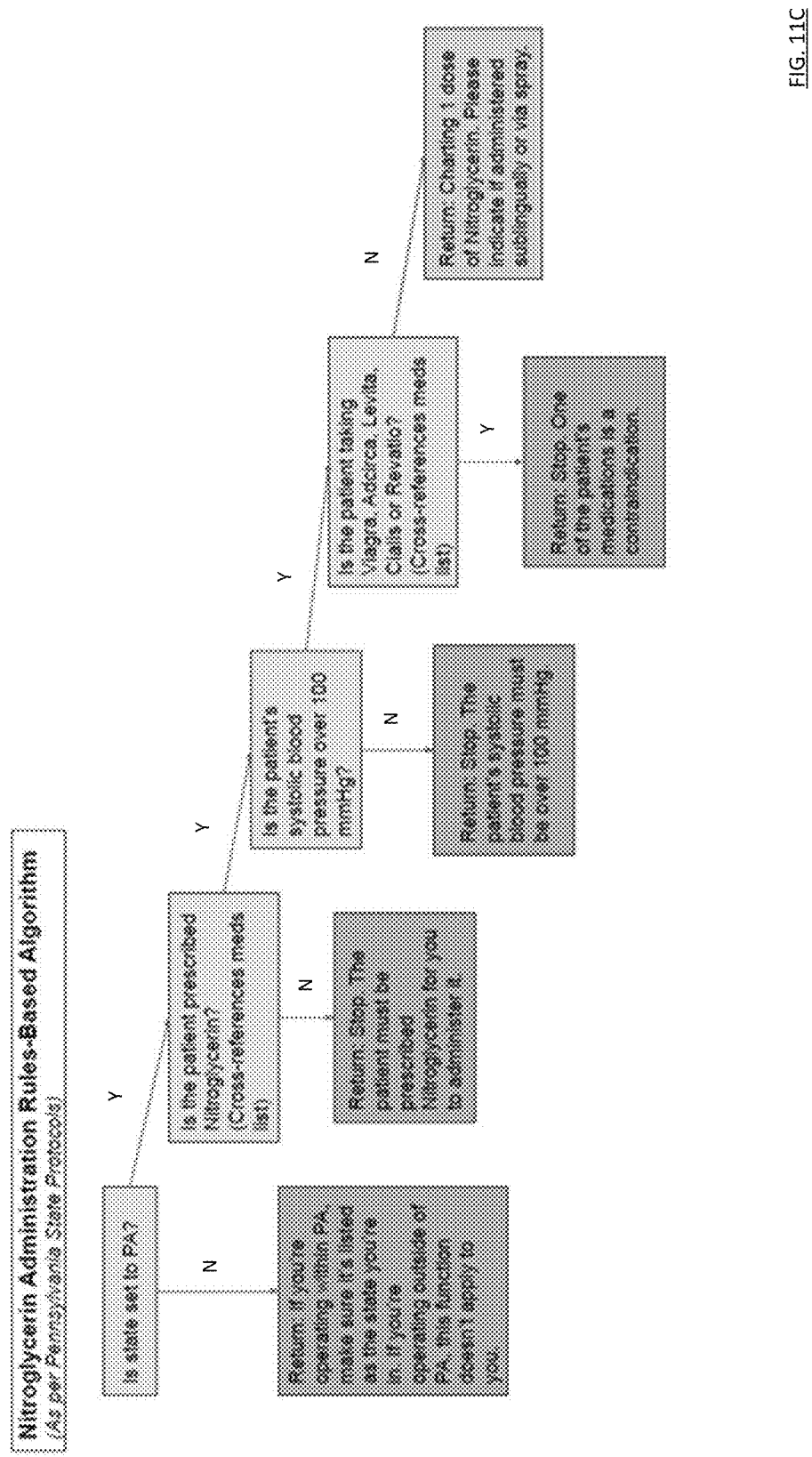
FIG. 11C includes a process flow diagram illustrating another example of the execution of a rules-based algorithm in accordance with certain embodiments of the invention.

FIG. 11B includes a process flow diagram illustrating an example of the execution of a rules-based algorithm module in accordance with certain embodiments of the invention. Rules-based algorithms may incorporate local, state and national guidelines regarding prehospital space health care protocols dependent on certain criteria as well as information, by way of example and not limited to, drug databases and real-time information regarding ED capacity. The rules-based algorithms can be configured to alert EMS personnel 204 to certain flags or indicators such as, but not limited to, significant deviations or drops in vitals, conditions, treatment options, contraindications to medications, comorbidities, and/or determining if a patient can refuse care, among other relevant indicators. FIG. 11B illustrates the process flow for one example of executing a rules-based algorithm module for determining contraindications for acetaminophen administration. In certain aspects, an alert can be triggered by the system 201 if there is a contraindication for administering the medicine, or a dosage instruction can be communicated if no contraindication is identified. FIG. 11C includes a process flow diagram illustrating another example of the execution of a rules-based algorithm module in accordance with certain embodiments of the invention. FIG. 11C illustrates the process flow for one example of executing a rules-based algorithm module for determining how and whether to administer nitroglycerine to a patient receiving emergency medical treatment.

Figure 12:
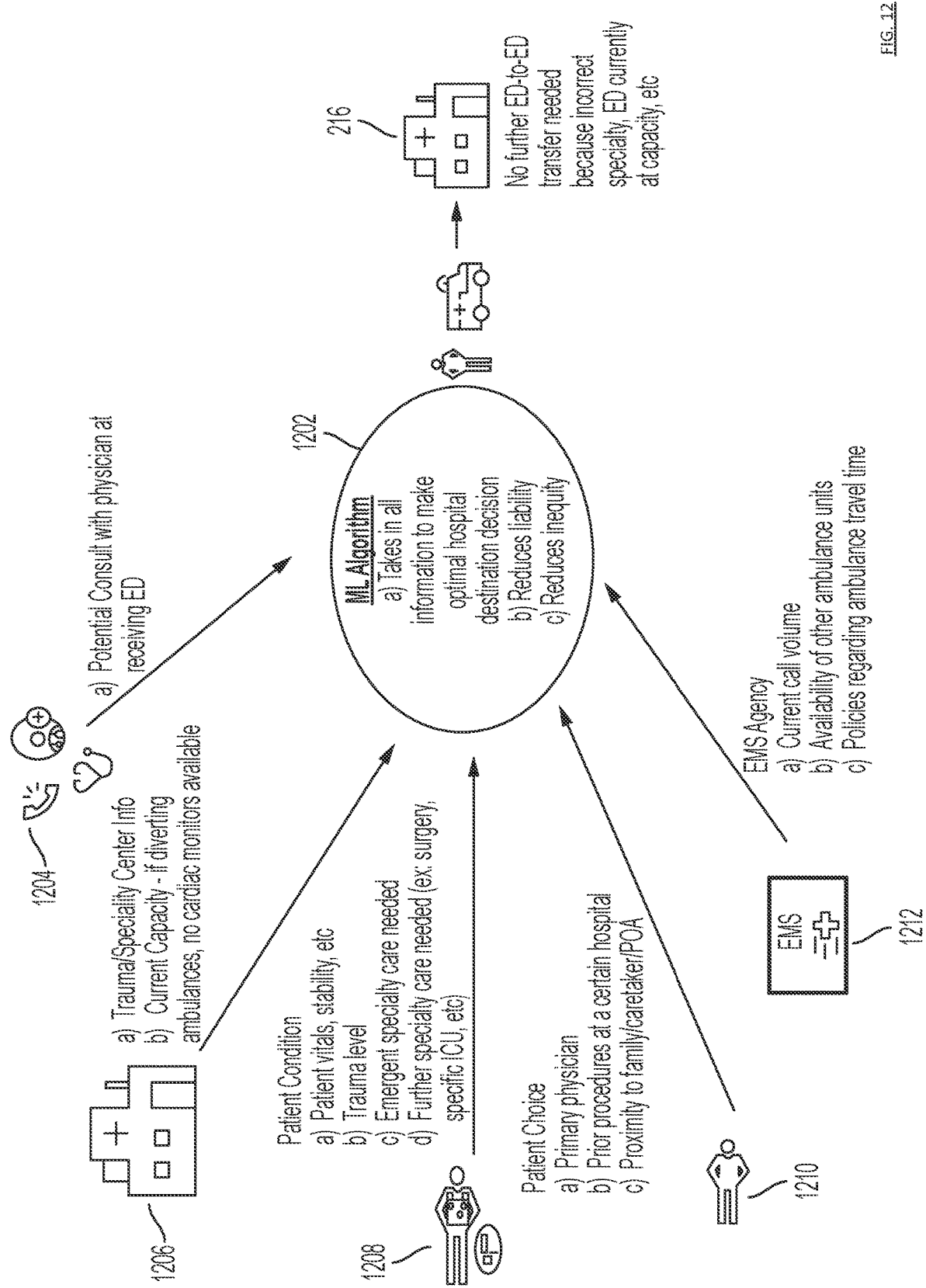
FIG. 12 depicts a combined process flow, data inputs, and computer system architecture diagram illustrating an example of the execution of a machine learning algorithm in accordance with certain embodiments of the invention.

FIG. 12 depicts a combined process flow and computer system architecture diagram illustrating an example of the execution of a machine learning or ML-based algorithm module 1202 configured in accordance with certain embodiments of the invention. In certain aspects, this diagram depicts the data sources that can be processed as part of determining an optimal hospital ED destination to avoid subsequent and potentially unnecessary ED-to-ED transfers. In addition to being unnecessary, certain ED-to-ED transfers can be expensive and typically delay necessary patient treatment. In various embodiments, ML-based algorithms can be used to process and make decisions with a high volume of information surrounding a patient including, for example and without limitation: continuous physiological vitals data, HL7 FHIR data (e.g., historical patient data), image data, audio data, and acoustical data, among other types of data and including data collected while on the emergency treatment site 202 and in transit to the medical facility 216. These data can be incorporated into models that can alert the EMS/prehospital team to acute situations, such as but not limited to, patient deterioration, best practices under certain conditions or medications, optimal ED destination, risk of stroke or heart attack, the need to send an alert to the ED of the medical facility 216, necessary ED trauma level, or required specialty care, among many others.

FIG. 12 illustrates examples of the various data sources and features, potentially including FHIR data, that could be incorporated into a ML algorithm that would aid in determining the optimal ED destination, for example, based on features such as physician consults 1204, hospital characteristics 1206, patient condition 1208, patient choice 1210, and/or EMS agency policies 1212 (e.g., EMS capacity or volume). In various embodiments, a module may be programmed for identifying a ranked list of potential healthcare facilities to which the patient can be transported from the emergency treatment site. Several objectives of this approach are to transport the patient to the most appropriate ED, to communicate any necessary alerts en route to the ED (e.g., sepsis, stroke, or other patient medical conditions), and to minimize unnecessary ED-to-ED transfers. In other aspects, it can be seen how these features can be used to mitigate potential human error or bias factors (e.g., age, sex, neighborhood, etc.) in prehospital care in areas such as, but not limited to, type of treatment provided, rate of detecting conditions, and selecting the most appropriate or optimal hospital destination.

FIG. 13 includes a table illustrating examples of various medical or health care situations to which a rules-based algorithmic approach and/or a machine learning algorithmic approach may be applied in connection with the various embodiments of the invention described herein.

Figure 14:
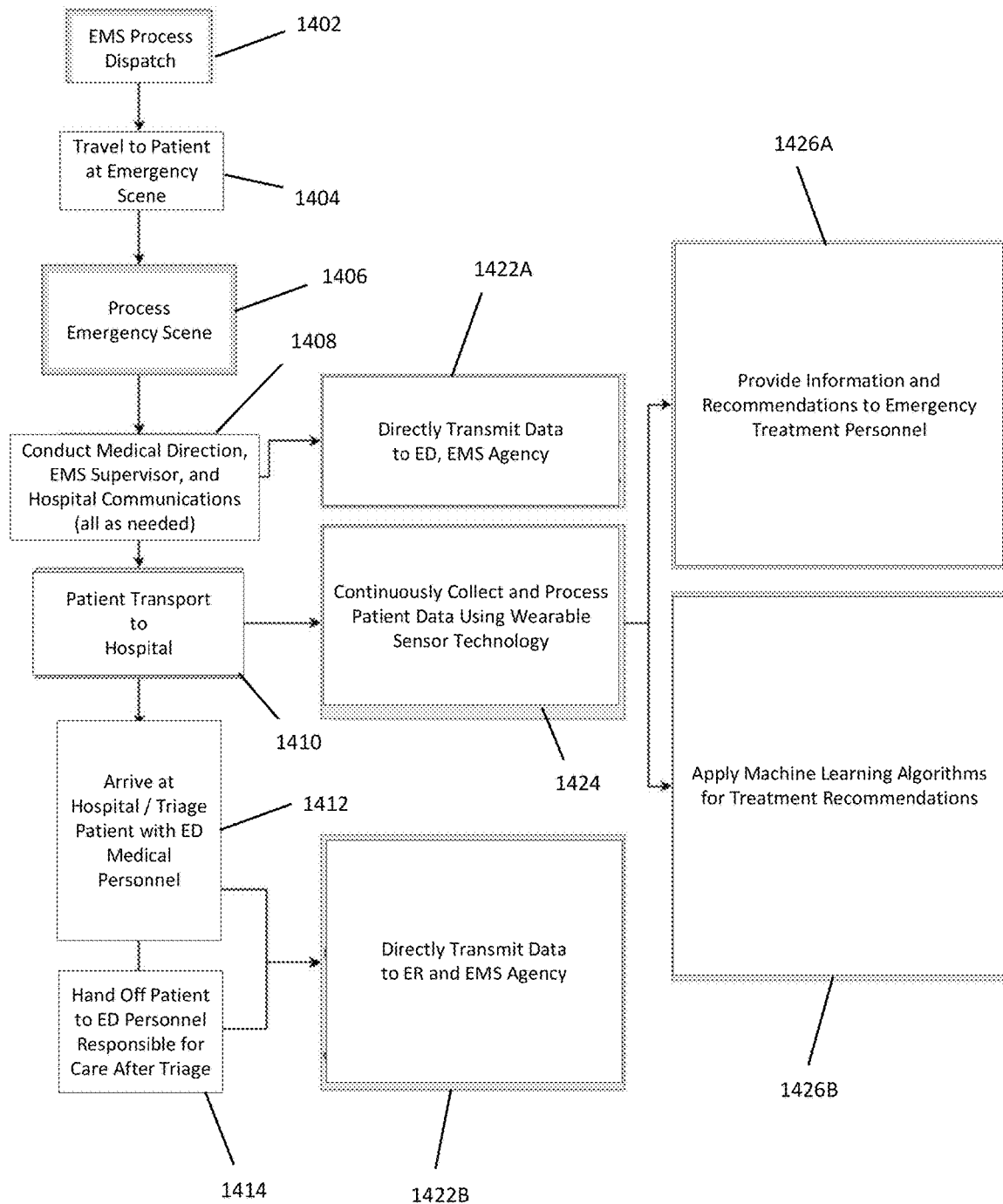
FIG. 14 includes a process flow diagram illustrating examples of opportunities for applying the tools and techniques associated with certain embodiments of the present invention to a process for providing emergency or prehospital medical treatment to a patient.

FIG. 14 includes a process flow diagram illustrating examples of opportunities for applying the tools and techniques associated with certain embodiments of the present invention to a process for providing emergency or prehospital medical treatment to a patient. Steps 1402 through 1414 illustrate a standard process for providing emergency medical treatment to a patient at an emergency scene. At step 1402, EMS personnel are dispatched to the emergency scene in response to a call for help for a patient or patients at the scene. At step 1404, the EMS personnel travel to the emergency scene, perhaps in an ambulance or other emergency vehicle. At step 1406, the EMS personnel process the emergency scene, including identifying and assisting victims (patients) at the scene, and assessing and treating their medical conditions. At step 1408, EMS personnel can communicate, as needed, to obtain medically related directions, to contact a supervisor, and/or to contact an ED of a hospital. These communications may continue as the patient is transported to the ED of a hospital at step 1410. At step 1412, a triage nurse at the ED can assess the patient to determine an appropriate course of medical treatment, prior to transferring responsibility to hospital or ED personnel at step 1414.

It can be seen how embodiments of the invention can assist with and enhance the standard processes associated with providing emergency medical treatment. For example, steps 1422A and 1422B represent those embodiments of the invention described herein which assist with patient data collection and processing as part of the various communications that can occur by and among EMS personnel, EMS agencies, physicians, call centers, and hospital ED departments. Step 1426 represents embodiments of the invention that can continuously gather and analyze data derived from the wearable sensor technology and techniques described herein, including during the process of transporting the patient to the hospital at step 1410, for example. Step 1426A represents how this collected and processed patient data can provide enhanced information and treatment recommendations to medical personnel. Step 1426B represents how this collected and processed patient data can be used to create machine learning algorithms to enhance treatment recommendations for the patient.

The examples presented herein can be intended to illustrate potential and specific implementations of the present invention. It can be appreciated that the examples can be intended primarily for purposes of illustration of the invention for those skilled in the art. No particular aspect or aspects of the examples can be necessarily intended to limit the scope of the present invention. For example, no particular aspect or aspects of the examples of system architectures, user interface layouts, algorithm use cases, or screen displays described herein can be necessarily intended to limit the scope of the invention.

It is to be understood that the figures and descriptions of the present invention have been simplified to illustrate elements that can be relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore, the invention as may be defined by such means-plus-function claims, resides in the fact that the functionalities provided by the various recited means can be combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual (e.g., cloud-based), permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth.

Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, processor, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to execution of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that can be located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, TypeScript, Ruby, PHP, and Perl. Various embodiments may be employed in a Lotus Notes environment, for example. Such software may be stored on any type of suitable computer-readable medium or media such as, for example, a magnetic or optical storage medium.

Thus, the execution and behavior of the embodiments can be described without specific reference to the actual software code. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, cellular network communication, power line communication, or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs) remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

As employed herein, an application server may be a server that hosts an API to expose business logic and business processes for use by other applications. Examples of application servers include J2EE or Java EE 5 (Oracle) application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java). Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture. Certain embodiments of the invention may employ web servers such as Apache web servers, for example.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Various embodiments may be described herein in the general context of computer executable instructions, such as software, program modules, and/or engines being executed by a computer. Generally, software, program modules, and/ or engines include any software element arranged to perform particular executions or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where executions can be performed by one or more remote processing devices that can be linked through a communications network. In a distributed computing environment, software, program modules, and/or engines may be located in both local and remote computer storage media including memory storage devices.

Although some embodiments may be illustrated and described as comprising functional components, software, engines, and/or modules performing various executions, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various executions of one or more embodiments. In various embodiments, for example, the article of manufacture may comprise a magnetic disk, optical disk, flash memory or firmware containing computer program instructions suitable for execution by an application specific processor.

Additionally, it is to be appreciated that the embodiments described herein illustrate example implementations, and that the functional elements, logical blocks, modules, and circuits elements may be implemented in various other ways which can be consistent with the described embodiments. Furthermore, the executions performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Reference to "one embodiment" or "an embodiment" means that a particular feature, structure, or characteristic described in connection with the embodiment is comprised in at least one embodiment. The appearances of the phrase "in one embodiment" or "in one aspect" in the specification can be not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms can be not necessarily intended as synonyms for each other. For example, some embodiments may be described using the terms "comlected" and/or "coupled" to indicate that two or more elements can be in direct physical or electrical contact with each other. The term "coupled," however, also may mean that two or more elements can be not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and can be comprised within the scope thereof. Furthermore, all examples and conditional language recited herein can be principally intended to aid the reader in understanding the principles described in the present disclosure and the concepts contributed to furthering the art, and can be to be construed as being without limitation to such specifically recited examples and conditions. Moreover, all statements herein reciting principles, aspects, and embodiments as well as specific examples thereof, can be intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by general purpose hardware as discussed above, as an alternative the same may also be embodied in dedicated hardware or a combination of software, hardware and/or dedicated hardware. If embodied in dedicated hardware, each can be implemented as a circuit or state machine that employs any one of or a combination of a number of technologies. These technologies may include, but can be not limited to, discrete logic circuits having logic gates for implementing various logic functions upon an application of one or more data signals, application specific integrated circuits having appropriate logic gates, or other components, etc. Such technologies can be generally well known by those of ordinary skill in the art and, consequently, can be not described in detail herein.

The flow charts and methods described herein show the functionality and execution of various implementations. If embodied in software, each block, step, or action may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s). Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be omitted or not performed. It is understood that all such variations can be within the scope of the present disclosure.

The terms "a" and "an" and "the" and similar referents used in the context of the present disclosure (especially in the context of the following claims) can be to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as though it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein can be not to be construed as limitations. Each group member may be referred to and claimed individually or in any combination with other members of the group or other elements found herein. It is anticipated that one or more members of a group may be comprised in, or deleted from, a group for reasons of convenience and/or patentability.

In various embodiments of the present invention, different types of artificial intelligence tools and techniques can be incorporated and implemented. Search and optimization tools including search algorithms, mathematical optimization, and evolutionary computation methods can be used for intelligently searching through many possible solutions. For example, logical operations can involve searching for a path that leads from premises to conclusions, where each step is the application of an inference rule. Planning algorithms can search through trees of goals and subgoals, attempting to find a path to a target goal, in a process called means-ends analysis.

Heuristics can be used that prioritize choices in favor of those more likely to reach a goal and to do so in a shorter number of steps. In some search methodologies heuristics can also serve to eliminate some choices unlikely to lead to a goal. Heuristics can supply a computer system with a best estimate for the path on which the solution lies. Heuristics can limit the search for solutions into a smaller sample size, thereby increasing overall computer system processing efficiency.

Propositional logic can be used which involves truth functions such as "or" and "not" search terms, and first-order logic can add quantifiers and predicates, and can express facts about objects, their properties, and their relationships with each other. Fuzzy logic assigns a degree of truth (e.g., between 0 and 1) to vague statements which may be too linguistically imprecise to be completely true or false. Default logics, non-monotonic logics and circumscription are forms of logic designed to help with default reasoning and the qualification problem. Several extensions of logic can be used to address specific domains of knowledge, such as description logics, situation calculus, event calculus and fluent calculus (for representing events and time), causal calculus, belief calculus (belief revision); and modal logics. Logic for modeling contradictory or inconsistent statements arising in multi-agent systems can also be used, such as paraconsistent logics.

Probabilistic methods can be applied for uncertain reasoning, such as Bayesian networks, hidden Markov models, Kalman filters, particle filters, decision theory, and utility theory. These tools and techniques help the system execute algorithms with incomplete or uncertain information. Bayesian networks are tools that can be used for various problems: reasoning (using the Bayesian inference algorithm), learning (using the expectation-maximization algorithm), planning (using decision networks), and perception (using dynamic Bayesian networks). Probabilistic algorithms can be used for filtering, prediction, smoothing and finding explanations for streams of data, helping perception systems to analyze processes that occur over time (e.g., hidden Markov models or Kalman filters). Artificial intelligence can use the concept of utility as a measure of how valuable something is to an intelligent agent. Mathematical tools can analyze how an agent can make choices and plan, using decision theory, decision analysis, and information value theory. These tools include models such as Markov decision processes, dynamic decision networks, game theory and mechanism design.

The artificial intelligence techniques applied to embodiments of the invention may leverage classifiers and controllers. Classifiers are functions that use pattern matching to determine a closest match. They can be tuned according to examples known as observations or patterns. In supervised learning, each pattern belongs to a certain predefined class which represents a decision to be made. All of the observations combined with their class labels are known as a data set. When a new observation is received, that observation is classified based on previous experience. A classifier can be trained in various ways; there are many statistical and machine learning approaches. The decision tree is one kind of symbolic machine learning algorithm. The naive Bayes classifier is one kind of classifier useful for its scalability, in particular. Neural networks can also be used for classification. Classifier performance depends in part on the characteristics of the data to be classified, such as the data set size, distribution of samples across classes, dimensionality, and the level of noise. Model-based classifiers perform optimally when the assumed model is an optimized fit for the actual data. Otherwise, if no matching model is available, and if accuracy (rather than speed or scalability) is a primary concern, then discriminative classifiers (e.g., SVM) can be used to enhance accuracy.

A neural network is an interconnected group of nodes which can be used in connection with various embodiments of the invention, such as execution of various methods, processes, or algorithms disclosed herein. Each neuron of the neural network can accept inputs from other neurons, each of which when activated casts a weighted vote for or against whether the first neuron should activate. Learning achieved by the network involves using an algorithm to adjust these weights based on the training data. For example, one algorithm increases the weight between two connected neurons when the activation of one triggers the successful activation of another. Neurons have a continuous spectrum of activation, and neurons can process inputs in a non-linear way rather than weighing straightforward votes. Neural networks can model complex relationships between inputs and outputs or find patterns in data. They can learn continuous functions and even digital logical operations. Neural networks can be viewed as a type of mathematical optimization which performs a gradient descent on a multi-dimensional topology that was created by training the network. Another type of algorithm is a backpropagation algorithm. Other examples of learning techniques for neural networks include Hebbian learning, group method of data handling (GMDH), or competitive learning. The main categories of networks are acyclic or feedforward neural networks (where the signal passes in only one direction), and recurrent neural networks (which allow feedback and short-term memories of previous input events). Examples of feedforward networks include perceptrons, multi-layer perceptrons, and radial basis networks.

Deep learning techniques applied to various embodiments of the invention can use several layers of neurons between the network's inputs and outputs. The multiple layers can progressively extract higher-level features from the raw input. For example, in image processing, lower layers may identify edges, while higher layers may identify the concepts relevant to a human such as digits or letters or faces. Deep learning may involve convolutional neural networks for many or all of its layers. In a convolutional layer, each neuron receives input from only a restricted area of the previous layer called the neuron's receptive field. This can substantially reduce the number of weighted connections between neurons. In a recurrent neural network, the signal will propagate through a layer more than once. A recurrent neural network (RNN) is another example of a deep learning technique which can be trained by gradient descent, for example.

While various embodiments of the invention have been described herein, it should be apparent, however, that various modifications, alterations, and adaptations to those embodiments may occur to persons skilled in the art with the attainment of some or all of the advantages of the present invention. The disclosed embodiments can be therefore intended to include all such modifications, alterations, and adaptations without departing from the scope and spirit of the present invention as claimed herein.

What is claimed is:

1. An emergency medical treatment system programmed for use in connection with providing medical treatment to a patient, the system comprising:
    a patient data display device programmed to receive and display data associated with the patient;
    an environmental assessment device configured to capture audio, video, or acoustical signals associated with an emergency treatment site associated with the patient;
    a patient monitoring device configured to be positioned on the patient and having multiple sensors programmed to collect physiological data or vitals data associated with the patient;
    a patient data processing device configured for:
        receiving sensor data from the patient monitoring device, and
        communicating the sensor data to the patient data display device;
    an artificial intelligence based algorithm module programmed for executing at least one artificial intelligence algorithm programmed for:
        receiving at least a portion of the sensor data collected by the patient monitoring device,
        communicating, to the patient data display device, data associated with at least one real-time change in vital physiological data of the patient,
        analyzing at least a portion of the received sensor data in comparison to at least a portion of historical health condition data associated with the patient,
        generating at least one recommended decision associated with treatment of the patient in response to analyzing the sensor data against the historical health condition data,
        generating at least one recommendation for a course of treatment for the patient in association with the patient data,
        generating the recommended treatment decision in connection with at least one local, state, and/or national guideline regarding a prehospital or emergency medical service health care protocol, and
        generating an alert associated with identification of at least one contraindication associated with the course of treatment for the patient in association with the patient data; and
    further comprising the system programmed for operation within a prehospital environment.

2. The system of claim 1, further comprising the patient monitoring device programmed for wirelessly transmitting patient data to the patient data display device and a computing environment.

3. The system of claim 2, further comprising the cloud computing environment programmed for communicating the patient data to at least one computer system associated with an emergency department of a healthcare facility.

4. The system of claim 3, further comprising the cloud computing environment programmed for communicating the patient data to at least one electronic health record computer system.

5. The system of claim 2, further comprising the cloud computing environment programmed for communicating the recommended decision to at least one computer system associated with an emergency department of a healthcare facility.

6. The system of claim 2, further comprising the cloud computing environment programmed for communicating the recommended decision to at least the patient data display device.

7. The system of claim 1, further comprising the patient data processing device including a speech-to-text module programmed for:
    converting audible speech into an audio file,
    parsing text from a text file derived from the audio file, and
    populating at least one data field of at least one form with the text parsed from the text file.

8. The system of claim 1, further comprising a rules-based algorithm module programmed for executing at least one rules-based algorithm for generating a communication in connection with at least one indicator determined by the rules-based algorithm in association with at least a portion of the patient data.

9. The system of claim 8, further comprising wherein generating the communication in connection with at least one indicator determined by the rules-based algorithm further comprises generating an alert.

10. The system of claim 8, wherein generating the communication in connection with at least one indicator determined by the rules-based algorithm further comprises generating a protocol-based recommendation.

11. The system of claim 1, wherein the patient monitoring device comprises a device wearable by a patient.

12. The system of claim 11, wherein the patient monitoring device comprises a vest.

13. The system of claim 1, wherein the environmental assessment device comprises a body camera.

14. The system of claim 1, wherein the emergency treatment site is located within a prehospital environment.

15. The system of claim 14, wherein the prehospital environment comprises at least one of a patient residence, a roadway, a vehicle accident location, a crime location, or a mass casualty incident location.

16. The system of claim 1, further comprising the patient display device programmed for receiving and transmitting HL7 FHIR compliant data communications.

17. The system of claim 1, further comprising the patient display device programmed for receiving or transmitting HL7 FHIR compliant data communications from or to at least one computer system operatively associated with an emergency medical care facility.

18. The system of claim 1, further comprising the patient display device programmed for receiving or transmitting HL7 FHIR compliant data communications from or to at least one computer system operatively associated with an emergency medical service.

19. The system of claim 1, further comprising a module programmed for communicating an identification of a comparatively higher risk patient situation associated with the patient data.

20. The system of claim 19, further comprising the module programmed for communicating an alert associated with the identification of the comparatively higher risk patient situation to at least one computing device of emergency medical personnel.

21. The system of claim 1, further comprising a module programmed for identifying a choice of healthcare facility to which the patient is to be transported from the emergency treatment site.

22. The system of claim 1, further comprising a module programmed for identifying a ranked list of potential healthcare facilities to which the patient can be transported from the emergency treatment site.

23. The system of claim 1, further comprising the patient data display device programmed for displaying at least one graphical representation of vitals data associated with the patient.

24. The system of claim 17, further comprising the module programmed for communicating an alert in response to at least one real-time change in the vital physiological data detected outside of a predetermined threshold or range.

25. The system of claim 24, further comprising the module programmed for communicating the real-time changes in the vital physiological data to the patient data display device.

26. The system of claim 24, further comprising the module programmed for communicating the real-time changes in the vital physiological data to at least one computer system of an emergency department of a healthcare facility located remotely from the emergency treatment site.

* * * * *